(12) United States Patent
Wang et al.

(10) Patent No.: US 8,728,339 B2
(45) Date of Patent: May 20, 2014

(54) BRANCHED SECONDARY ALCOHOL ALKOXYLATE SURFACTANTS FOR TEXTILE PROCESSING

(75) Inventors: Xiao Hua Wang, Shanghai (CN); Wanglin Yu, Pearland, TX (US); Shawn J. Maynard, Angleton, TX (US)

(73) Assignee: Dow Global Technologies LLC, Midland, MI (US)

( * ) Notice: Subject to any disclaimer, the term of this patent is extended or adjusted under 35 U.S.C. 154(b) by 18 days.

(21) Appl. No.: 13/701,684

(22) PCT Filed: Jun. 30, 2010

(86) PCT No.: PCT/CN2010/074824
§ 371 (c)(1),
(2), (4) Date: Dec. 3, 2012

(87) PCT Pub. No.: WO2012/000189
PCT Pub. Date: Jan. 5, 2012

(65) Prior Publication Data
US 2013/0131386 A1  May 23, 2013

(51) Int. Cl.
*D06M 15/53* (2006.01)
(52) U.S. Cl.
USPC .......................... 252/8.63; 252/8.91; 8/115.6
(58) Field of Classification Search
USPC ................................ 564/495; 252/8.63, 8.91
See application file for complete search history.

(56) References Cited

U.S. PATENT DOCUMENTS

| | | | | |
|---|---|---|---|---|
| 3,546,298 A | * | 12/1970 | Tindall | 564/495 |
| 3,560,575 A | * | 2/1971 | Tindall | 568/712 |
| 3,651,144 A | * | 3/1972 | Tindall | 564/495 |
| 4,067,905 A | * | 1/1978 | Adrian et al. | 564/495 |
| 5,198,209 A | | 3/1993 | Zhou et al. | |
| 5,573,694 A | | 11/1996 | Danner | |
| 6,017,875 A | | 1/2000 | Kadono et al. | |
| 6,087,317 A | | 7/2000 | Gee | |
| 6,143,038 A | | 11/2000 | Yamamoto et al. | |
| 6,177,481 B1 | | 1/2001 | Grape et al. | |
| 6,255,275 B1 | | 7/2001 | Kadono et al. | |
| 6,346,509 B1 | | 2/2002 | Kadono et al. | |
| 6,429,342 B1 | | 8/2002 | Clement et al. | |
| 6,908,524 B2 | | 6/2005 | Goldstein et al. | |
| 6,974,520 B2 | | 12/2005 | Goldstein et al. | |
| 7,361,362 B2 | | 4/2008 | Bamba | |
| 2004/0067211 A1 | | 4/2004 | Bamba | |
| 2006/0130990 A1 | | 6/2006 | Arfaoui et al. | |

FOREIGN PATENT DOCUMENTS

| | | |
|---|---|---|
| DE | 4131551 A1 | 3/1993 |
| EP | 487735 A1 | 12/1991 |
| EP | 850907 A2 | 7/1998 |
| EP | 1396535 A1 | 10/2004 |
| JP | 63203877 A | 8/1988 |
| JP | 03135432 | 6/1991 |
| JP | 11349507 | 12/1999 |
| JP | 2002129481 | 5/2002 |
| JP | 2003096674 | 4/2003 |
| JP | 2005298689 | 10/2005 |
| JP | 2007131992 | 5/2007 |
| JP | 2007308615 | 11/2007 |
| WO | 9404259 | 3/1994 |

* cited by examiner

*Primary Examiner* — Brian J Davis

(57) ABSTRACT

Provided is a composition that is useful for textile processing, including for softening and providing smoothness to textiles. The composition comprises an alkoxylate of the formula (I): wherein AO, EO, m, n, R. $R^1$ and $R^2$ are as defined below, and a polysiloxane oil.

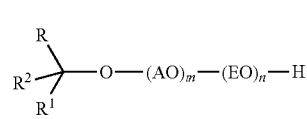

(I)

12 Claims, No Drawings

BRANCHED SECONDARY ALCOHOL ALKOXYLATE SURFACTANTS FOR TEXTILE PROCESSING

CROSS REFERENCE TO RELATED APPLICATIONS

This application is a 35 USC §371 national phase filing of PCT/CN2010/074824 filed Jun. 30, 2010.

FIELD OF THE INVENTION

The invention relates to new branched secondary alcohol alkoxylates, to compositions thereof, and to their use in textile processing.

BACKGROUND OF THE INVENTION

Polysiloxanes are used in the textile processing industry as finishing agents for improving various properties of the textile, such as smoothness and softness. Typically, the polysiloxanes are employed in the form of oil-in-water emulsions, prepared by emulsification of a polysiloxane using a surfactant as an emulsifying agent.

In addition to functioning as an emulsifying agent, it is desirable for the surfactant to impart other useful properties to the emulsion, such as rapid wetting and penetration of the textile. In addition, low foam is also important in order to avoid emulsion breakage and undesirable accumulation of polysiloxane deposits on the textile. A common problem in the industry, however, is that emulsifying agents often cannot meet all these attributes simultaneously. The industry, therefore, attempts to address this shortcoming in various ways, including by increasing the concentration of the emulsifying agent, using a co-solvent or using other types of non-silicone softeners.

These alternative approaches exhibit a number of their own disadvantages, which include increased cost as well as degradation of performance. The alternative approaches, therefore, are often inadequate for meeting the needs of the industry. New emulsifying agents that can serve multiple useful roles in textile processing would be a significant advance for the industry.

BRIEF SUMMARY OF THE INVENTION

In one aspect, the invention provides a composition. The composition comprises: (a) an alkoxylate of formula I:

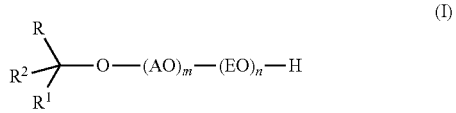

wherein AO, m, n, R, $R^1$, $R^2$ are as defined below; and (b) a polysiloxane oil.

In another aspect, the invention provides a method for treating and processing textile materials. The method comprises contacting the textile materials with a composition as described herein.

DETAILED DESCRIPTION OF THE INVENTION

As noted above, in a first aspect the invention provides a composition. The composition contains a polysiloxane oil together with an emulsifying agent. The emulsifying agents described herein are novel materials that provide a number of favorable properties, for instance, effective emulsification to silicones, good stability of the formed silicone emulsions, low foaming, and good wetting and penetrating. Compositions of the invention are therefore well suited for use in the textile processing industry.

The emulsifying agent is an alkoxylate of the formula I:

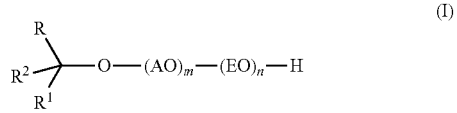

wherein AO is an alkyleneoxy containing at least 3 carbon atoms; EO is ethyleneoxy; m is 1-6; n is 1-40; R and $R^1$ are independently $C_1$-$C_{14}$ alkyl; and $R^2$ is H or $C_1$-$C_{13}$ alkyl, wherein the group formed by R, $R^1$, $R^2$ and the carbon to which they are attached contains 7 to 16 carbon atoms and has a branching degree of at least 3.

Alkoxylates of formula I prepared as described below have been surprisingly discovered to exhibit a narrow molecular weight distribution, represented by the materials' polydispersity index (weight average molecular weight/number average molecular weight (Mw/Mn) as determined by gel permeation chromatography). In addition, the alkoxylates also contain surprisingly low levels of residual unreacted alcohols. As a result, it is believed that the narrow molecular weight distribution, low residual alcohol content, as well as the highly branched nature of the alkoxylates results in materials that provide overall improved performance.

In some embodiments, the polydispersity index (PDI) of the alkoxylates of formula I is 1.15 or less, alternatively 1.1 or less. In some embodiments, the compositions contain 3 weight percent or less, alternatively 2 weight percent or less, alternatively 1 weight percent or less, or alternatively 0.5 weight percent or less of residual alcohols.

In the alkoxylates of formula I, AO represents an alkyleneoxy group containing at least 3 carbon atoms. In some embodiments, AO is butyleneoxy (BO). In some embodiments, AO is propyleneoxy (PO).

Formula I includes variables "m" and "n" that describe the molar ratio of charged reagents. The reaction product produced between the reaction of the alcohol and the alkyleneoxy containing at least 3 carbon atoms, or the adduct thereof and the ethylene oxide is a distribution of oligomers that have on average the molar ratio of the charged reagents. Individually, "m" and "n" represent molar ratios of, respectively, alkoxylation with an alkyleneoxy containing at least 3 carbon atoms and ethoxylation. In some embodiments of the invention m is at least 1, alternatively at least 2. In some embodiments, m is 5 or less, alternatively 4 or less, or alternatively, 3 or less. In some embodiments, m falls in the range of 1 to 5, alternatively 2 to 5.

In some embodiments, n is at least 2, alternatively at least 3, alternatively at least 4, or alternatively at least 5. In some embodiments, n is 30 or less, alternatively 20 or less, or alternatively 10 or less. In some embodiments, n falls in the range 2 to 10, alternatively 3 to 9, or alternatively 5 to 9.

In the formula I alkoxylates, R, $R^1$, $R^2$ and the carbon to which they are attached form a group that is the organic residue of the highly branched secondary alcohol used to make the alkoxylate. In general, the group contains between 7 and 16 carbon atoms. In some embodiments, the group contains between 9 and 12 carbon atoms. The group also has a branching degree of 3 or more. In some embodiments of the invention, the branching degree is 4 or more. The term "branching degree" as used herein means the total number of methyl (—CH$_3$) groups minus 1. For instance, if there are four methyl groups, then the branching degree is 3. In some embodiments, compounds in which simultaneously R$^1$ is CH$_3$(CH$_2$)$_2$CH(C$_2$H$_5$)(CH$_2$)$_2$CH(CH$_3$)—, and R$^2$ is H, and R is CH$_3$ are excluded as alkoxylates of the invention (i.e., compounds prepared from (3-methyl-6-ethyl)-2-nonanol as the secondary alcohol).

In some embodiments of the invention, R is C$_3$-C$_{12}$ alkyl, alternatively C$_3$-C$_8$ alkyl, or alternatively C$_4$-C$_6$ alkyl. In some embodiments, R contains at least 2 methyl groups.

In some embodiments of the invention. R$^1$ is C$_3$-C$_{12}$ alkyl, alternatively C$_4$-C$_{10}$ alkyl, or alternatively C$_6$-C$_8$ alkyl. In some embodiments, R$^1$ contains at least 2 methyl groups.

In some embodiments of the invention, R$^2$ is C$_1$-C$_3$ alkyl. In some embodiments, R$^2$ is H.

In some embodiments of the invention, the alkoxylate is of the formula II:

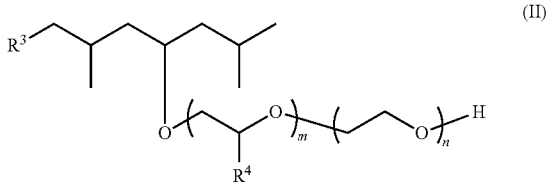

wherein R$^3$ is H or iso-propyl and R$^4$ is CH$_3$ or CH$_2$CH$_3$, and m and n are as defined above.

In some embodiments of the invention, the alkoxylate is of the formula:

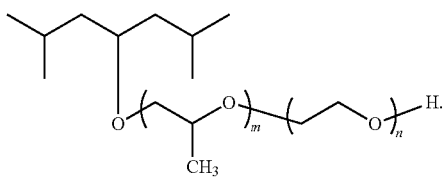

wherein m and n are as defined above.

In some embodiments, the alkoxylate is of the formula:

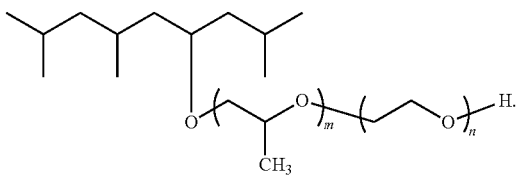

wherein m and n are as defined above.

Alkoxylates of formula I may be prepared by a process, as described herein, that yields materials having narrow molecular weight distribution and low residual alcohol content. According to the process, a highly branched secondary alcohol is reacted with an alkylene oxide compound containing 3 or more carbon atoms, followed by ethylene oxide, under alkoxylation conditions. The catalyst used for the alkoxylations is a double metal cyanide compound.

The highly branched secondary alcohol is a compound containing 7 to 16 carbon atoms, a branching degree of 3 or more, and one hydroxy group. In some embodiments, the compound contains between 9 and 12 carbon atoms. In some embodiments, the branching degree is 4 or more. Examples of suitable secondary alcohols include 2,6,8-trimethyl-4-nonanol, and 2,6-dimethyl heptan-4-ol. In some embodiments, the alcohol (3-methyl-6-ethyl)-2-nonanol is excluded from the process.

Prior to the alkoxylation reaction, it may be advantageous to dry the starting alcohol in order to reduce its water content. Known techniques may be used, including for instance application of reduced pressure, elevated temperature, nitrogen purge, or a combination of these. The water content may be reduced to, for example, 300 ppm or less, alternatively 200 ppm or less, or alternatively 100 ppm or less, or alternatively 50 ppm or less, or alternatively 25 ppm or less.

The alkylene oxide compound containing 3 or more carbon atoms is reacted with the alcohol under alkoxylation conditions. In a non-limiting embodiment illustrative of suitable alkoxylation conditions, this reaction may be carried out at an elevated temperature or temperatures ranging from about 80° C. to about 180° C. In other non-limiting embodiments, the temperature may range from about 100° C. to about 160° C. Pressures from about 14 psia to about 60 psia may, in certain non-limiting embodiments, be particularly efficacious, but other pressures may also be effectively employed. Those skilled in the art will be able to determine appropriate conditions with, at most, routine experimentation.

Following the alkoxylation with the alkylene oxide compound containing 3 or more carbon atoms, the product is then ethoxylated with ethylene oxide. As with the initial alkoxylation, this reaction may also be carried out at an elevated temperature or temperatures ranging from about 80° C. to about 180° C. or, for instance, from about 100° C. to about 160° C. Pressures from about 14 psia to about 60 psia may, in certain non-limiting embodiments, be particularly efficacious, but other pressures may also be effectively employed.

The alkoxylation and ethoxylation reactions are conducted in the presence of an effective amount of a double metal cyanide compound as catalyst. The amount of the catalyst may, in some embodiments, range from about 0.0001 percent to about 0.1 percent by weight, based on the total charge of alcohol and oxides. Suitable double metal cyanide catalysts include those described in U.S. Pat. No. 6,429,342, which is incorporated herein by reference. By way of example, a catalyst comprising Zn$_3$[Co(CN)$_6$]$_2$ may be used.

Following the alkoxylation reactions, the product may be discharged from the reactor and used as is, or it may be further processed or purified by techniques well known to those skilled in the art. For instance, the product may be filtered.

Alkoxylates of formula I function as emulsifying agents for polysiloxane oils (also referred to as silicone oils). In this role, the alkoxylates of formula I form part of a composition that comprises the alkoxylate together with an polysiloxane oil. As noted earlier, such compositions are useful in textile processing, for instance for imparting softness and smoothness to textiles.

Any of the polysiloxane oils known in the art for use in textile processing are suitable in the compositions of the invention. Non-limiting examples of such oils include: aminofunctionalized silicone oil, amidofunctional silicone, dimethylsilicone oil, and hydroxyfunctional silicone. The amount of the alkoxylate of formula I relative to the organopolysiloxane oil in the composition may be in the range from 5 to 100 parts by weight, alternatively from 15 to 75 parts by weight, or alternatively from 20 to 50 parts by weight, per 100 parts by weight of the organopolysiloxane oil.

The composition of the invention may be provided in the form of a concentrate, which may be particularly suitable for reducing storage and transportation costs. Prior to use in textile processing, the composition is typically formulated as an oil in water emulsion. The amount of water used for the preparation of the emulsion may be readily determined by a person of ordinary skill in the art. Typically, the amount should be large enough to yield an emulsion, but as small as possible for ease of handling, storage, and transportation. By way of example, the amount of water may be in the range from 20 to 2000 parts by weight, alternatively from 80 to 800 parts by weight, or alternatively from 100 to 500 parts by weight per 100 parts by weight of the organopolysiloxane oil.

The emulsion may be prepared using techniques known to those skilled in the art. By way of example, the polysiloxane oil, alkoxylate of formula I, and water may be introduced together into a vessel in their desired amounts, or a mixture of the organopolysiloxane oil and the alkoxylate introduced into a vessel followed by the addition of water, and the components mixed and agitated using a suitable stirrer, such as a propeller mixer, blade stirrer, disk stirrer, or different types of homogenizers. Other materials may be added to the mixture including, for instance, acetic acid and/or sodium carbonate, e.g., for adjusting the composition to a desirable pH; other surfactants, including anionic, nonionic, and cationic surfactants.

The emulsion of the invention may be further diluted with water prior to use, for instance at 10 to 100 times dilution. Any suitable method, such as spraying, dipping or kiss roll application may be used for application of the composition to the textile. Following treatment, the textile may be dried, for instance by heating at 80 to 180° C.

The composition of the invention may be used for treating a wide variety of textile materials, including natural fibers such as cotton, flax, silk and wool; synthetic fibers such as polyester, polyamide, polyacrylonitrile, polyethylene, polypropylene and polyurethane; and inorganic fibers such as glass fiber and carbon fiber. The form of the textile materials is not critical and includes threads, woven and non-woven fabrics, filaments, rovings, knit cloths, and the like.

The following examples are illustrative of the invention but are not intended to limit its scope. Unless otherwise indicated, the ratios, percentages, parts, and the like used herein are by weight.

EXAMPLES

Examples 1-3

Synthesis and Characterization of Alkoxylates of Formula I

Raw Materials 2,6,8-Trimethylnonan-4-ol (TMN) and 2,6-dimethyl heptan-4-ol (diisobutyl carbinol or DIBC) are supplied by The Dow Chemical Company.

Double metal cyanide (DMC) catalyst (Lot # P2D5000171), is manufactured and supplied by Bayer.

Ethylene Oxide (EO), propylene oxide (PO), and butylene oxide (BO) are supplied by The Dow Chemical Company.

Manufacturing Equipment

DMC catalyzed surfactant samples are prepared using a semi-batch process in a 2 gallon, stirred, baffled, jacketed reactor.

Property Test Methods

Conventional GPC is used for general molecular weight analysis. Reported results are relative to linear polyethylene glycol standards, shown below. Polymer Laboratories PEG-10 Polyethylene glycol standards are used with $3^{rd}$ order fitting. Molecular weight ($M_n$, $M_w$, $M_z$) is measured with an Agilent 1100 system equipped with a Polymer Labs Mixed E column coupled to a Differential Refractive Index (RI) detector operated at 40° C. The chromatographic mobile phase is tetrahydrofuran (THF). Each sample (100 ul, 25.00 mg/mL) is dissolved in THF, injected twice, and eluted at 1.0 mL/min.

The amount of unreacted alcohol in alkoxylate samples is determined by gas chromatography. External alcohol standards dissolved in methanol are used. The standard stock solution (0.016-11.249% (w/w)) is prepared by weighing the alcohol (0.06 g-1.01 g) and methanol (10 g) into a glass vial. Low concentrations are created by dilution of existing samples (0.64% (w/w)). Alkoxylate samples are prepared by dilution in methanol by mass to achieve the desired concentration. The alcohol concentration data reported are from single injections.

Example 1

TMN/PO/EO Alkoxylate Surfactants

The alkoxylate was prepared by first forming the PO-TMN adduct by reaction between PO and TMN in the presence of the DMC catalyst followed by reaction between EO and the PO-alcohol adduct. TMN alcohol was stripped at 80° C. under vacuum with nitrogen sweep until the water content reaches less than 200 ppm (24 ppm). DMC catalyst (0.126 g) is then slurried in 1250 g of the dried starter alcohol (TMN). The TMN Alcohol/DMC catalyst slurry is charged to a 9-liter alkoxylation reactor and purged with nitrogen. The reactor is sealed and pressured with nitrogen to 16-20 psia, then heated with agitation to reaction temperature (130° C.). The DMC catalyst is activated with 210 g of PO at 130° C., and then 555 g PO (765 g total) are added continuously (5 g/min) with stirring followed by a 2 hr digest period (130° C.) to consume residual oxide. A sample (100 g) is removed from the reactor and measured for hydroxyl analysis (5.546% hydroxyl or 307 molecular weight corresponding to the 2 mole propoxylate). To the remaining PO-alcohol adduct 1110 g of EO is added at (5 g/min) with stirring at 130° C. followed by a 2 hr digestion period (130° C.) with intermediate sampling (200 g). This is followed by a second ethylene oxide (775 g) feed, digest, and intermediate sampling (221 g). A third ethylene oxide (450 g) feed and digest affords the alkoxylate product, TMN/2PO/9EO (the hydroxyl content is 2.420% or 702 molecular weight by hydroxyl analysis, corresponding to the foregoing formula). As listed in Table 1, the TMN/2PO/9EO sample contains 1.3 wt % of unreacted alcohol residue and has PDI at 1.07.

Following the same procedure, other TMN/PO/EO products are prepared as listed in Table 1. All the samples contain less than 2 wt % unreacted alcohol residue and show PDI of less than 1.15.

TABLE 1

Property Results for TMN Ethoxylates and Alkoxylates

| Description | Un-reacted TMN (wt %) | Mw (GPC) | PDI |
|---|---|---|---|
| TMN/2PO/7EO | 1.9 | 746 | 1.09 |
| TMN/2PO/9EO | 1.3 | 805 | 1.07 |
| TMN/5PO/5EO | 0.4 | 785 | 1.06 |
| TMN/5PO/7EO | 0.2 | 857 | 1.05 |
| TMN/5PO/9EO | 0.1 | 930 | 1.04 |

Example 2

DIBC/PO/EO Alkoxylate Surfactants

The alkoxylate is prepared by first forming the PO-DIBC adduct by reaction between PO and DIBC in the presence of the DMC catalyst followed by reaction between EO and the PO-alcohol adduct. DIBC is stripped at 90° C. under vacuum with nitrogen sweep until water content is less than 200 ppm (27 ppm). DMC catalyst (0.24 g) is slurried in 621 g of the dehydrated starter alcohol (DIBC). The DIBC/DMC catalyst slurry is charged to a 9 liter alkoxylation reactor and purged with nitrogen. The reactor is sealed and pressured with nitrogen to 16-20 psia, then heated with agitation to reaction temperature (130° C.). The DMC catalyst is activated with 195 g of PO at 130° C. under 20 psia nitrogen, and then 810 g PO (1,005 g total) is added continuously (5 g/min) with stirring followed by a 70 minute digest period (130° C.) to consume residual oxide. An intermediate sample (105 g) is removed for hydroxyl analysis (4.600% OH or 370 molecular weight corresponding to the four mole propoxylate). To the remaining PO-alcohol adduct 1,320 g of EO is added at (5 g/min) with stirring at 130° C. followed by a 60 min digestion period (130° C.) with intermediate sampling (453 g). After a second ethylene oxide (445 g) feed and digest period, the reaction product is sampled for hydroxyl analysis: 2.181% hydroxyl or 779 molecular weight, corresponding to the alkoxylate product DIBC/4PO/9EO. As listed in Table 2, the DIBC/4PO/9EO sample contains 0.2 wt % of unreacted alcohol residue and has a PDI at 1.05.

Example 3

DIBC/PO/EO Alkoxylate Surfactants (DIBC/4PO/10EO)

As in the previous example, the alkoxylate is prepared by first forming the PO-DIBC adduct by reaction between PO and DIBC in the presence of the DMC catalyst followed by reaction between EO and the PO-alcohol adduct. DIBC is stripped at 90° C. under vacuum with nitrogen sweep until water content is less than 200 ppm (27 ppm). DMC catalyst (0.24 g) is slurried in 620 g of the dehydrated starter alcohol (DIBC). The DIBC/DMC catalyst slurry is charged to a 9 liter alkoxylation reactor and purged with nitrogen. The reactor is sealed and pressured with nitrogen to 16-20 psia, then heated with agitation to reaction temperature (130° C.). The DMC catalyst is activated with 185 g of PO at 130° C. under 20 psia nitrogen, and then 815 g PO (1,000 g total) is added continuously (3-5 g/min) with stirring followed by a digest period (130° C.) to consume residual oxide. An intermediate sample (120 g) is removed for hydroxyl analysis (4.416% OH or 385 molecular weight corresponding to the four mole propoxylate). To the remaining PO-alcohol adduct 1,250 g of EO is added at (3-5 g/min) with stirring at 130° C. followed by a digestion period (130° C.) with intermediate sampling (480 g). After a second ethylene oxide (425 g) feed and digest period, the reaction product is sampled for hydroxyl analysis: 2.098% hydroxyl or 810 molecular weight, corresponding to the alkoxylate product DIBC/4PO/10EO. As listed in Table 2, the DIBC/4PO/10EO sample contains 0.1 wt % of unreacted alcohol residue and has a PDI at 1.05.

Following the same procedure, other DIBC/PO/EO and DIBC/BO/EO products are prepared as listed in Table 2. All the samples contain less than 2 wt % unreacted alcohol residue and exhibit a PDI of less than 1.15. The samples show good surface tension reduction capability and low contact angles with the selected samples.

TABLE 2

Property Results for DIBC Alkoxylates

| Description | Unreacted DIBC (wt %) | Mw (GPC) | Pd |
|---|---|---|---|
| DIBC/10EO | 1.1 | 658 | 1.04 |
| DIBC/4PO/3EO | 0.3 | 603 | 1.07 |
| DIBC/4PO/7EO | 0.2 | 887 | 1.06 |
| DIBC/4PO/10EO | 0.1 | 989 | 1.05 |
| DIBC/2BO/3EO | 0.7 | 549 | 1.11 |
| DIBC/2BO/5EO | 0.4 | 651 | 1.13 |
| DIBC/2BO/6EO | 0.3 | 698 | 1.12 |
| DIBC/2BO/7EO | 0.3 | 728 | 1.12 |
| DIBC/2BO/10EO | 0.2 | 868 | 1.11 |

Examples 4-5

Evaluation of Alkoxylates of Formula I

In the following Examples 3-5, surfactants of the invention having the following structure are tested:

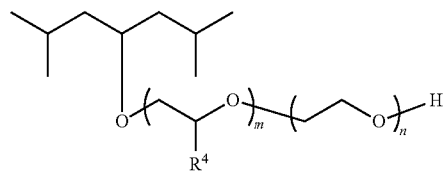

Inventive surfactant 1: $m=4$, $R^4=\!-\!CH_3$, $n=3$
Inventive surfactant 2: $m=4$, $R^4=\!-\!CH_3$, $n=10$
Inventive surfactant 3: $m=4$, $R^4=\!-\!CH_3$, $n=7$
Inventive surfactant 4: $m=2$, $R^4=\!-\!CH_2CH_3$, $n=10$
Inventive surfactant 5: $m=2$, $R^4=\!-\!CH_2CH_3$, $n=7$ The following comparative surfactants are also evaluated:

MULTISO™ 13/30 and MULTISO™13/90 are commercial products from Sasol, which are ethoxylated isotridecanol to average 3 moles and 9 moles, respectively, on each alcohol starter.

SOFTANOL™ 30 and SOFTANOL™90 are commercial products from Nippon Sakuba, which are ethoxylated C11-C15 secondary alcohols with the average EO moles on each alcohol as 3 and 9, respectively.

TERGITOL™ TMN-3, TERGITOL™ TMN-6 and TERGITOL™ TMN-10 are Dow commercial products. They are ethoxylated 2,6,8-Trimethylnonan-4-ol (TMN) with 3, 8, and 11 average EO moles on each alcohol, respectively.

Example 4

Penetrating Performance Comparison

Test Methods

The test is carried out at room temperature (22° C.±1) according to a method based on China Industry Standard HG/T 2575-94 (Surface active agents-determination of penetrating power by immersion). The test method involves the following steps:

Preparation of surfactant solutions: prepare surfactant solution using distilled water (or deionized water). The surfactant concentration is based on the test conditions, typically 0.15% and 0.3% by weight. Put the surfactant solution 800 ml in 1000 ml beaker.

Evaluation of the penetrating power: place the standard cotton fabric piece (circle cotton canvas with a diameter of 35 mm and weight of 0.38-0.39 g) on the surface center point of the surfactant solution, at the same time, starting the stopwatch. The solution will penetrate into the fabric piece gradually. Stop the stopwatch at the moment when the standard cotton fabric piece begins to sink in the surfactant solution and record the time. The measured time is referred to as penetrating time. The test for each surfactant composition under examination is repeated 10 times and the mean is reported as the test result. If surfactant solution is turbid, no values are measured.

Test Data

Penetrating time of inventive and comparative examples at different concentrations is shown in Table 3. Shorter penetrating time indicates better penetrating performance.

TABLE 3

Test data of penetrating time.

| Example | | Penetrating time(s) | |
| --- | --- | --- | --- |
| | | 1.5 g/L | 3.0 g/L |
| Inventive Example 1 | Inventive surfactant 1/Inventive surfactant 2 (w/w:1/1) | 17.8 | 5.0 |
| Comparative Example 1 | SOFTANOL ™ 30/ SOFTANOL ™ 90 (w/w:1/1) | 21.3 | 12.0 |
| Comparative Example 2 | MULTISO ™ 13/30/ MULTISO ™ 13/90 (w/w:1/1) | 37.8 | 14.7 |
| Comparative Example 3 | TERGITOL ™ TMN-3/ TERGITOL ™ TMN-10 (w/w:1/1) | 22.4 | 13.5 |

Conclusion

From test data in Table 3, it can be concluded that the Inventive example shows better penetrating performance than comparative examples.

Example 5

Emulsify Silicone

In this Example, various emulsions containing a polysiloxane oil and an alkoxylate of formula I are tested. The tested formulations are shown in the following tables. Abbreviations are as follows: Silyou 1100 silicone and Dow Corning AP-8040 silicone are commercial silicone based oils available from, respectively, Wacker-Dymatic and Dow Corning Corporation. LUTENSOL™ XP30 and LUTENSOL™ XP90 are surfactants based on C10-Guerbet alcohol ethoxylates. They are available from BASF. HOAc is acetic acid.

| Inventive example 1-1 | | Inventive example 1-2 | |
| --- | --- | --- | --- |
| Silyou 1100 silicone | 10 g | Silyou 1100 silicone | 10 g |
| HOAc(5% aq. sol) | 0.6 g | HOAc(5% aq. sol) | 0.6 g |
| DI water | 45 g | DI water | 45 g |
| Inventive surfactant 1 | 4.5 g | Inventive surfactant 1 | 4.0 g |
| Inventive surfactant 2 | 0.5 g | Inventive surfactant 2 | 1.0 g |

| Inventive example 1-3 | | Inventive example 1-4 | |
| --- | --- | --- | --- |
| Silyou 1100 silicone | 10 g | Silyou 1100 silicone | 10 g |
| HOAc(5%) | 0.6 g | HOAc(5%) | 0.6 g |
| DI water | 45 g | DI water | 45 g |
| Inventive surfactant 1 | 3.5 g | Inventive surfactant 1 | 3.0 g |
| Inventive surfactant 2 | 1.5 g | Inventive surfactant 2 | 2.0 g |

| Comparative example 1-1 | | Comparative example 1-2 | |
| --- | --- | --- | --- |
| Silyou 1100 silicone | 10 g | Silyou 1100 silicone | 10 g |
| HOAc(5%) | 0.6 g | HOAc(5%) | 0.6 g |
| DI water | 45 g | DI water | 45 g |
| MULTISO ™ 13/30 | 3.5 g | MULTISO ™ 13/30 | 3.0 g |
| MULTISO ™ 13/90 | 1.5 g | MULTISO ™ 13/90 | 2.0 g |

| Comparative example 1-3 | |
| --- | --- |
| Silyou 1100 silicone | 10 g |
| HOAc(5%) | 0.6 g |
| DI water | 45 g |
| MULTISO ™ 13/30 | 2.5 g |
| MULTISO ™ 13/90 | 2.5 g |

| Inventive example 2-1 | | Inventive example 2-2 | |
| --- | --- | --- | --- |
| Dow Corning AP-8040 silicone | 15 g | Dow Corning AP-8040 silicone | 15 g |
| HOAc(5%) | 1 g | HOAc(5%) | 1 g |
| DI water | 75 g | DI water | 75 g |
| Inventive surfactant 1 | 6.3 g | Inventive surfactant 1 | 5.6 g |
| Inventive surfactant 2 | 0.7 g | Inventive surfactant 2 | 1.4 g |

| Inventive example 2-3 | |
| --- | --- |
| Dow Corning AP-8040 silicone | 15 g |
| HOAc(5%) | 1 g |
| DI water | 75 g |
| Inventive surfactant 1 | 4.9 g |
| Inventive surfactant 2 | 2.1 g |

| Comparative example 2-1 | | Comparative example 2-2 | |
| --- | --- | --- | --- |
| Dow Corning AP-8040 silicone | 15 g | Dow Corning AP-8040 silicone | 15 g |
| HOAc(5%) | 1 g | HOAc(5%) | 1 g |
| DI water | 75 g | DI water | 75 g |
| MULTISO ™ 13/30 | 6.3 g | MULTISO ™ 13/30 | 5.6 g |
| MULTISO ™ 13/90 | 0.7 g | MULTISO ™ 13/90 | 1.4 g |

| Comparative example 2-3 | | Comparative example 2-4 | |
| --- | --- | --- | --- |
| Dow Corning AP-8040 silicone | 15 g | Dow Corning AP-8040 silicone | 15 g |
| HOAc(5%) | 1 g | HOAc(5%) | 1 g |

-continued

| Comparative example 2-3 | | Comparative example 2-4 | |
|---|---|---|---|
| DI water | 75 g | DI water | 75 g |
| MULTISO ™ 13/30 | 4.9 g | LUTENSOL ™ XP30 | 6.3 g |
| MULTISO ™ 13/90 | 2.1 g | LUTENSOL ™ XP90 | 0.9 g |

| Comparative example 2-5 | | Comparative example 2-6 | |
|---|---|---|---|
| Dow Corning AP-8040 silicone | 15 g | Dow Corning AP-8040 silicone | 15 g |
| HOAc(5%) | 1 g | HOAc(5%) | 1 g |
| DI water | 75 g | DI water | 75 g |
| LUTENSOL ™ XP30 | 4.2 g | LUTENSOL ™ XP30 | 5.6 g |
| LUTENSOL ™ XP90 | 2.8 g | LUTENSOL ™ XP90 | 1.4 g |

| Comparative example 2-7 | |
|---|---|
| Dow Corning AP-8040 silicone | 15 g |
| HOAc(5%) | 1 g |
| DI water | 75 g |
| LUTENSOL ™ XP30 | 4.9 g |
| LUTENSOL ™ XP90 | 2.1 g |

Process to Emulsify Silicone

The emulsification process is as follows. The surfactants and silicone oil are added into a 250 ml three-bottled flask, and stirred with an electric mixing propeller until the mixture is mixed well. Then 5% HOAc solution is added while stirring, and the mixture mixed until uniform. With continued stirring, water is added very slowly, especially at the period of phase inversion. During the whole process of adding water, the mixture is stirred to uniformity before another addition of water. After the addition of water, stirring is stopped and the pH of the mixture is check. If the pH is outside the range of 5.5 to about 6.5, 5.0% HOAc solution or 5.0% $Na_2CO_3$ solution are added to adjust the pH to the 5.5-6.5 range. The final silicon emulsion is then poured into a 100 ml wide-mouth clear glass bottle and the appearance of the silicone emulsion is observed, within the day and after 5 days.

Evaluation of the Silicon Emulsion

The silicone emulsion is inspected visually by the naked eye. The appearance of the emulsion is ranked as clear, transparent or semi-transparent, which each indicate that the silicone is emulsified well and acceptable emulsion is obtained; hazy or cloudy, which indicate the silicon emulsion is emulsified but less effectively; milky, turbid, or phase separated, which indicate the emulsifier can not emulsify the silicone effectively. Results are shown in Table 4.

TABLE 4

| | Appearance of silicon mixture at time | |
|---|---|---|
| | Appearance of silicone mixture at indicated time | |
| Formulation | Within one day | After 5 days |
| Inventive example 1-1 | ± | ± |
| Inventive example 1-2 | + | + |
| Inventive example 1-3 | + | + |
| Inventive example 1-4 | + | + |
| Comparative example 1-1 | − | − |
| Comparative example 1-2 | + | + |
| Comparative example 1-3 | − | − |
| Inventive example 2-1 | − | − |
| Inventive example 2-2 | + | + |
| Inventive example 2-3 | + | + |
| Comparative example 2-1 | − | − |
| Comparative example 2-2 | ± | ± |
| Comparative example 2-3 | − | − |
| Comparative example 2-4 | + | − |
| Comparative example 2-5 | + | − |
| Comparative example 2-6 | − | − |

"+" = clear, transparent, or semi-transparent; "±" = hazy or cloudy; "−" = turbid or milky white.

The data in Table 4 shows that compared to the comparative emulsifiers, the inventive surfactants can better emulsify the silicone oils and result in more stable emulsions.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A composition comprising:
   (a) an alkoxylate of formula I:

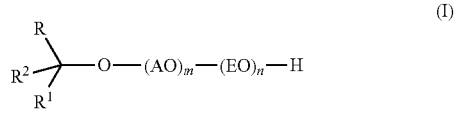

(I)

wherein AO is an alkyleneoxy containing at least 3 carbon atoms; EO is ethyleneoxy; m is 1-6; n is 1-40; R and $R^1$ are independently $C_1$-$C_{14}$ alkyl; and $R^2$ is H or $C_1$-$C_{13}$ alkyl, wherein the group formed by R, $R^1$, $R^2$ and the carbon to which they are attached contains 7 to 16 carbon atoms and has a branching degree of at least 3; and
   (b) a polysiloxane oil.

2. A composition according to claim 1 wherein the polydispersity index of the alkoxylate is 1.15 or less.

3. A composition according to claim 1 wherein the composition comprises no more than 2 percent by weight of residual alcohol.

4. A composition according to claim 1 wherein AO is propyleneoxy or butyleneoxy.

5. A composition according to claim 1 wherein the group formed by R, $R^1$, $R^2$ and the carbon to which they are attached contains 9 to 12 carbon atoms.

6. A composition according to claim 1 wherein the alkoxylate is of formula II:

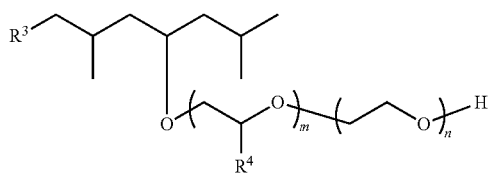

(II)

wherein $R^3$ is H or iso-propyl and $R^4$ is $CH_3$ or $CH_2CH_3$.

7. A composition according to claim 1 wherein the polysiloxane oil is aminofunctionalized silicone oil, amidofunctional silicone, dimethylsilicone oil, or hydroxyfunctional silicone.

8. A composition according to claim 1 where the composition is in the form of a concentrate.

9. A composition according to claim 1 where the composition further comprises water and is the form of an emulsion.

10. A composition according to claim 9 comprising 5 to 100 parts by weight of the alkoxylate and 20 to 2000 parts by weight of water, based on 100 parts by weight of the polysiloxane oil.

11. A method for treating and processing textile materials which comprises contacting the textile materials with a composition according to claim 1.

12. A textile treated by the method of claim 11.

* * * * *